(12) United States Patent
Orejola et al.

(10) Patent No.: US 9,192,702 B2
(45) Date of Patent: Nov. 24, 2015

(54) AUTONOMOUS ARTIFICIAL HEART

(71) Applicants: Wilmo C Orejola, Pompton Plains, NJ (US); Cedric A Orejola, Pawcatuck, CT (US)

(72) Inventors: Wilmo C Orejola, Pompton Plains, NJ (US); Cedric A Orejola, Pawcatuck, CT (US)

(*) Notice: Subject to any disclaimer, the term of this patent is extended or adjusted under 35 U.S.C. 154(b) by 0 days.

(21) Appl. No.: 14/299,048

(22) Filed: Jun. 9, 2014

(65) Prior Publication Data

US 2014/0371849 A1 Dec. 18, 2014

Related U.S. Application Data

(60) Provisional application No. 61/956,565, filed on Jun. 12, 2013.

(51) Int. Cl.
*A61M 1/10* (2006.01)
*A61M 1/12* (2006.01)

(52) U.S. Cl.
CPC ............. *A61M 1/101* (2013.01); *A61M 1/1086* (2013.01); *A61M 1/1098* (2014.02); *A61M 1/12* (2013.01)

(58) Field of Classification Search
CPC ........ A61M 1/10; A61M 1/101; A61M 1/1086
USPC ................. 623/3.16, 3.17, 3.18, 3.19, 3.2
See application file for complete search history.

(56) References Cited

U.S. PATENT DOCUMENTS

| 3,919,722 | A | * | 11/1975 | Harmison | 623/3.16 |
| 5,300,111 | A | * | 4/1994 | Panton et al. | 623/3.19 |
| 8,419,789 | B2 | * | 4/2013 | Shu et al. | 623/3.1 |
| 2002/0116055 | A1 | * | 8/2002 | Snyder | 623/3.18 |
| 2014/0371849 | A1 | * | 12/2014 | Orejola et al. | 623/3.13 |

* cited by examiner

*Primary Examiner* — Bruce E Snow
(74) *Attorney, Agent, or Firm* — Michael J. Feigin, Esq.; Feigin & Associates, LLC

(57) ABSTRACT

Embodiments of the disclosed technology are directed to a self-contained, totally implantable blood pump that replaces the whole heart. It is a small spherical device that encloses all of its blood propulsion dynamics. The dynamics are controlled by a built-in microcontroller that regulates the speed of the motor in response to hemodynamic changes like blood pressure fluctuations, level of body activity, and/or posture. The hemodynamic changes are detected using a plurality of sensors disposed around the body. An implantable transcutaneously rechargeable battery provides power to the microcontroller, motor and/or sensors.

7 Claims, 14 Drawing Sheets

AUTONOMOUS ARTIFICIAL HEART

BACKGROUND OF THE DISCLOSED TECHNOLOGY

Heart disease is the leading cause of death in the United States, accounting for more deaths than all forms of cancer combined. Heart failure—the most common, costly, disabling and deadly of heart ailments—affects close to five million people in the United States, and each year about 550,000 new cases are diagnosed. The mortality rate is approximately 40,000 a year, but heart failure is listed as a contributing cause of 280,000 deaths every year. It is also the leading cause for hospitalization in people older than 65. Of more concern is the fact that more than 50% of patients seek re-admission within six months after treatment, and the average duration of hospital stays is six days. Its health care cost in the United States. is estimated to be more than $35 billion.

Heart failure can be treated medically. However, many patients in advanced stages of heart failure do not respond to medications. Heart transplantation is the ultimate remedy. About 60,000 end-stage heart failure patients may benefit from heart transplantation, but only 2,100 receive heart transplants annually because of limited availability of organs. Totally artificial hearts could save more patients from donor heart shortage.

Medical devices have been used safely and effectively to assist the failing heart and the circulation. There are many assist devices already available, including ventricular assist devices (VAD) and totally artificial hearts (TAH). VAD's continue to play a role as temporary circulatory support, bridge-to-heart transplantation or, for some devices, destination therapy (traveling to a remote location for medical services).

There are various forms of VADs. They are classified as to how a VAD is used (LVAD, RVAD or BiVAD); where a VAD is located (extracorporeal or implantable); or how its pump works (pulsatile or continuous flow). Although FDA-approved for clinical uses, presently available designs are still prone to serious complications, such as infection, bleeding and stroke. Cables being inserted through the skin become sources of infection because batteries and controls worn outside the body drive these devices. Heparin anticoagulation is a requirement for most of these devices. Excessive anticoagulation causes bleeding, while inadequate anticoagulation can lead to strokes.

(5) This invention is a self-contained and totally implantable blood pump that replaces the whole heart. This mechanical heart and the controls, including the power source, are self-contained and totally implanted inside the body. There are no external cables or connections. The hemodynamic benefit is achieved and controlled by the built-in microcontroller that makes the heart autonomously adjust to blood pressure, physical activity and/or body posture.

SUMMARY OF THE EMBODIMENTS

Embodiments of the disclosed technology are directed to a self-contained, totally implantable blood pump that replaces the whole heart. It is a small spherical device that encloses all its blood propulsion dynamics. The dynamics are controlled by a built-in microcontroller, which regulates the speed of the motor in response to hemodynamic changes (such as blood pressure fluctuations), body activity (such as walking) or posture (such as lying down or standing). An implantable transcutaneously rechargeable battery provides the power.

In an embodiment of the disclosed technology, an artificial heart has an artificial right ventricle, and an artificial left ventricle within a housing. The artificial heart may have one or more of the following components: a) a first inflow port corresponding to an entrance into said artificial right ventricle from right atrium; b) a second inflow port corresponding to an entrance into said artificial left ventricle from the left atrium; c) a first outflow port corresponding to an exit to the pulmonary artery; d) a second outflow port corresponding to an exit to the aorta; and e) a microcontroller operatively coupled with said housing of the artificial heart.

The microcontroller further connects to at least two of the following sensors: a) a pressure sensor placed at a location near the proximal aorta, wherein said location is limited to where pressure at said second outflow port is measurable; b) an orientation sensor; c) a vibration sensor; and/or d) a temperature sensor.

In a further embodiment, the artificial heart has tri-leaflet, flexible plastic valves that open to allow one direction of flow at the inflow ports into the artificial ventricles and at the outflow ports out of the artificial ventricle. Still further, the artificial heart may have two separate woven Dacron rims attached around each inflow valve and projected outward forming a sleeve, wherein said sleeve is adapted for suturing remnants of an organic right atrium and an organic left atrium.

Still further, the artificial heart may have first and second woven Dacron tubes. Each tube may have a proximal end. The proximal end of the first tube surrounds the first outflow port and the proximal end of the second tube surrounds the second outflow port.

The artificial heart may also have a rotating longitudinal member located at a vertical central axis of the housing, extending from a plane which intersects with the first and second inflow and outflow ports to a bottom of an internal cavity within the artificial heart. This rotating longitudinal member extends between two elastic membranes of the opposing artificial right and left ventricles.

The rotating longitudinal member may also connect with a shaft of a motor outside the housing. The longitudinal rotating member may rotate a complete turn based upon data received by the microcontroller. Still further, the rotation may have a propulsion phase equal to one half of the time of a resting phase. During the resting phase, blood flows into at least one of the internal membranes.

In still a further embodiment of the disclosed technology, the receipt of data by the microcontroller from the pressure sensor indicates that a threshold level of pressure has been crossed, causing the rotating of the longitudinal rotating member. Further, the receipt of data by the microcontroller from the temperature sensor, indicating that a threshold level of temperature has been crossed, modifies the threshold level of pressure received by the microcontroller, which causes the rotating of the longitudinal member. The temperature sensor may be, for example, disposed under the skin near the artificial heart housing, in order to accurately measure temperature.

In a further embodiment of the artificial heart, the receipt of data by the microcontroller from the orientation sensor, indicating that a person is lying down, causes a less frequent rotation of the longitudinal member, and indicating that a person is standing up, causes more frequent rotation of the longitudinal member, wherein the less and the more are relative to each other. Still further, the receipt of data by the microcontroller from the vibration sensor, indicating that a threshold level of vibration or muscle movement like walking has been crossed, modifies the threshold level of pressure received by the microcontroller, which causes the rotating of the longitudinal member. The vibration sensor may be, for example, disposed at or near the hips of an individual to detect movement.

In a further embodiment of the disclosed technology, an artificial heart has a microcontroller pacemaker, the pacemaker activating a systole in the artificial heart, based on the receipt of data from sensors. The sensors may include one or more of the following: a) a pressure sensor; b) an orientation sensor; c) a vibration sensor; and/or d) a temperature sensor. The systole may be activated after a passage of a pre-determined amount of time and a determination that the pumping of blood from the heart to the body is timely, based on input from at least one the sensor.

In a further embodiment, the microcontroller sets the rate of a systole at a default rate in the absence of stimuli to the contrary, and begins to return the rate of the systole to the default rate upon the absence of stimuli. The default rate corresponds to a 100 RPM (revolution per minute) of rotation of the longitudinal member.

The pressure sensor measures pressure in an ascending aorta directly or indirectly, and pressure below a pre-defined threshold causes the determination to be made to increase the rotation of the longitudinal rotating member and increase pumping volume. Pressure above a pre-defined threshold causes the determination to be made to decrease or increase the rotation of the longitudinal member and increase pumping volume.

In further embodiments of the artificial heart, the detection of an upright orientation, as detected by the orientation sensor, causes a systole to be activated more frequently than in a lying down orientation. Increased vibration, as detected by the vibration sensor, causes a systole to be activated more frequently up to the predetermined minimum amount of time between pumping. Still further, increased temperature, as detected by the temperature sensor, causes the systole to be activated more frequently. The frequency may yield a minimum amount of time between pumping.

DETAILED DESCRIPTION OF EMBODIMENTS
OF THE DISCLOSED TECHNOLOGY

The presently disclosed technology is a self-contained, totally implantable blood pump that replaces the whole heart. It is a small spherical device that encloses all its blood propulsion dynamics. The dynamics are controlled by a built-in microcontroller that regulates the speed of the motor in response to hemodynamic changes, such as blood pressure fluctuations, body activity (walking), or posture (lying down or standing). An implantable, transcutaneously rechargeable battery provides the power.

Embodiments of the disclosed technology will become clearer in view of the description of the following figures.

Figure 1:
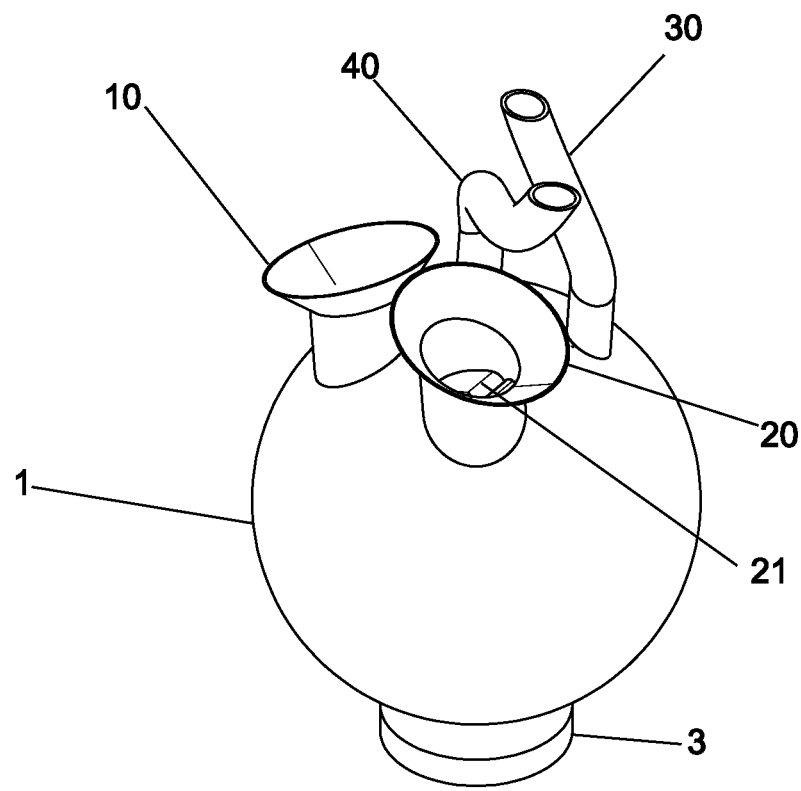
FIG. 1 shows a perspective assembled view of an artificial autonomous heart, according to an embodiment of the disclosed technology.

FIG. 1 shows a perspective assembled view of an artificial autonomous heart, according to an embodiment of the disclosed technology.

The artificial autonomous heart is formed generally of a spherical body 1. For purposes of this specification, the terms "sphere 1," "body 1," "artificial autonomous heart 1," and/or "artificial heart 1" may be used interchangeably to generally refer to the artificial autonomous heart and/or the body of the user, as used in context. Inside the sphere 1 is a rotating core. It propels blood into the hemispheric ventricles, which are separated by elastic membranes or sacs provided with inflow valves 10, 20, and outflow valves 30, 40, at the base to ensure unidirectional flow.

The two hemispheric ventricles have a clamshell-design, which makes one a mirror image of the other. The membrane is the only interface between the device and the blood. Blood in both domes fills in the sac when the two arched turbines of the rotating core pass the membranes during the cycle, equivalent of diastole. Blood in the sac is ejected simultaneously through their outflow valves. The arched turbines of the rotating core push the membranes against the domes squeezing the blood volume out of the ventricles, equivalent of a systole. The device could eject up to 100 ml of blood every cycle, equivalent of a stroke volume.

Fluid or lubricating fluid around the rotating core facilitates a frictionless movement of its turbines against the membranes. The moving core is uniformly stabilized during rotation at a base 3 and apex 9 by ball bearings. The shaft of the turbines is engaged with the rotor of the brushless DC motor. The motion of the shaft is described further in subsequent figures.

Built into the configuration of the spherical device is the microcontroller that controls the speed or RPMs (revolutions per minute) of the motor, which is programmed at 100 rpms. The RPMs respond to the actuators or potentiometer that, in turn, respond or adjust to the microcontroller, which is programmed to receive electronic input from pressure, tilt or vibration sensors. A totally implantable 9 to 12-volt lithium polymer battery supplies the power to the brushless DC motor. It is implanted just beneath skin on the chest to facilitate transcutaneous recharging.

Referring still to FIG. 1, artificial heart body 1 has at least four valves extending therefrom. The mitral valve 10 and the tricuspid valve 20 represent and perform the function of their corresponding counterparts in a human heart. These valves control the flow of blood into the left and right ventricles of the artificial heart.

Figure 2:
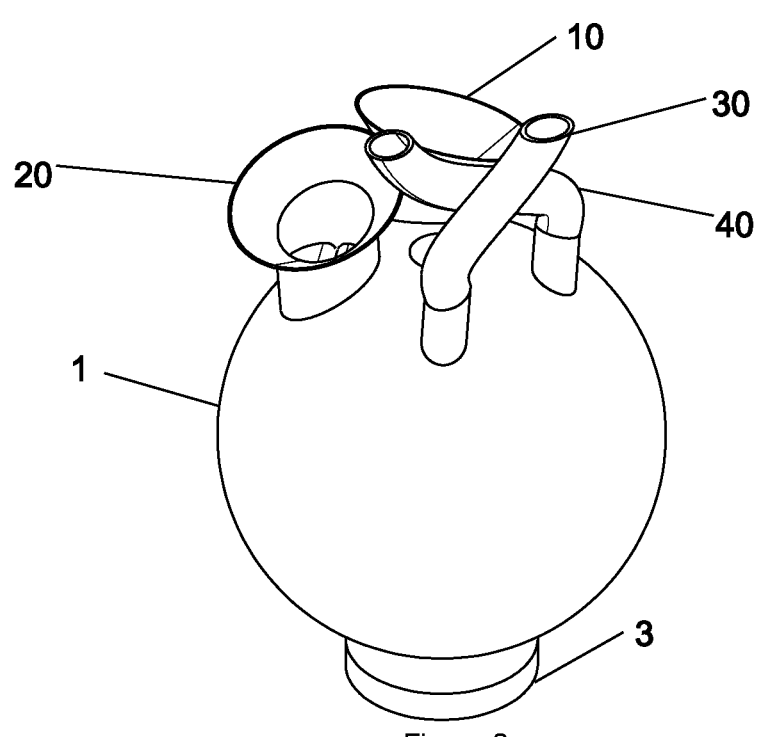
FIG. 2 shows a back perspective view of the artificial autonomous heart of FIG. 1.

FIG. 2 shows a back perspective view of the artificial autonomous heart of FIG. 1. The pulmonic valve 30 and the aortic valve 40 control the flow of blood out of the artificial heart 1.

Figure 3:
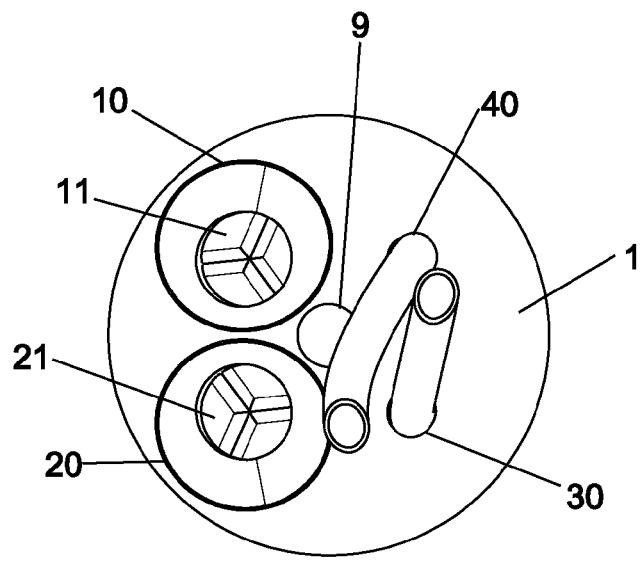
FIG. 3 shows a top view of the artificial autonomous heart, according to an embodiment of the disclosed technology.
Figure 4:
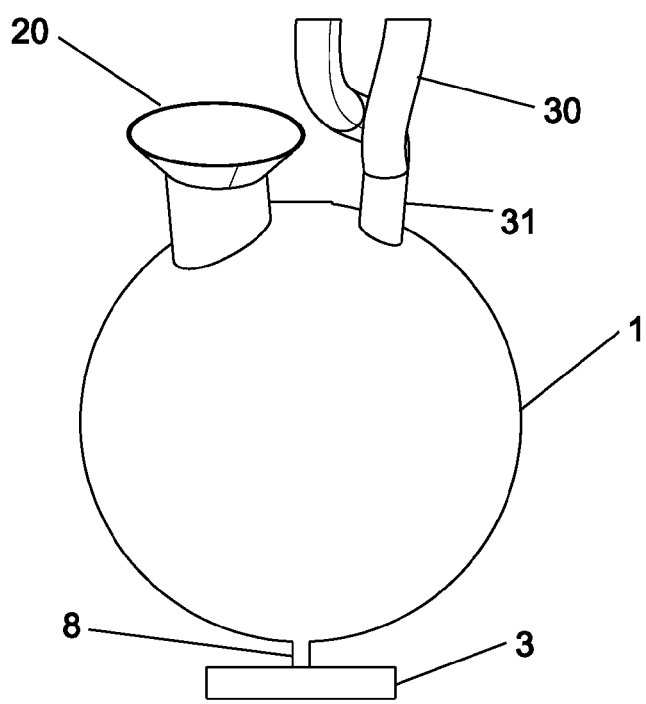
FIG. 4 shows a side elevation view of the artificial autonomous heart, according to an embodiment of the disclosed technology.

FIG. 3 shows a top view of the artificial autonomous heart, according to an embodiment of the disclosed technology. FIG. 4 shows a side elevation view of the artificial autonomous heart, according to an embodiment of the disclosed technology. A ball-bearing stabilizer 9 is shown at the top, center-point of the sphere. A rotating core assembly comprises a two-arched turbine and scalloping inter-space, a shaft 8, which one end engages with ball-bearing stabilizer 9 and the rotor of the brushless motor 3 on the opposite end. The shaft 8 is shown in FIG. 4 extending from the bottom of the sphere 1. The shaft 8 is coupled to a motor 3 disposed at a lower extremity of the sphere 1.

Figure 5:
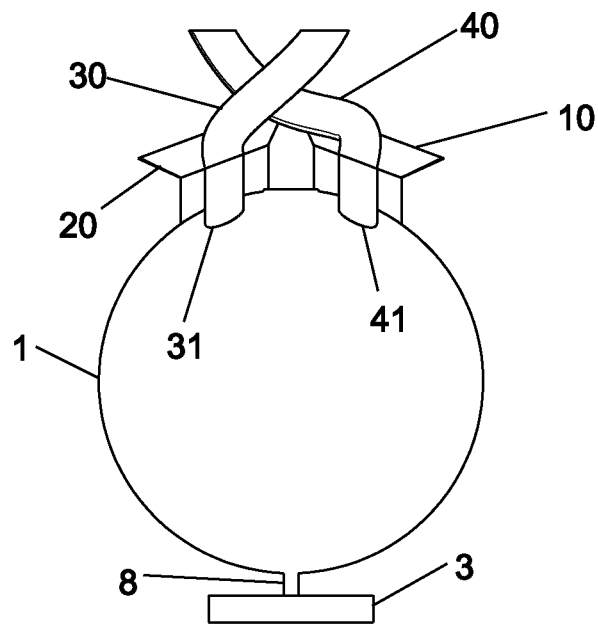
FIG. 5 shows a front elevation view of the artificial autonomous heart, according to an embodiment of the disclosed technology.
Figure 6:
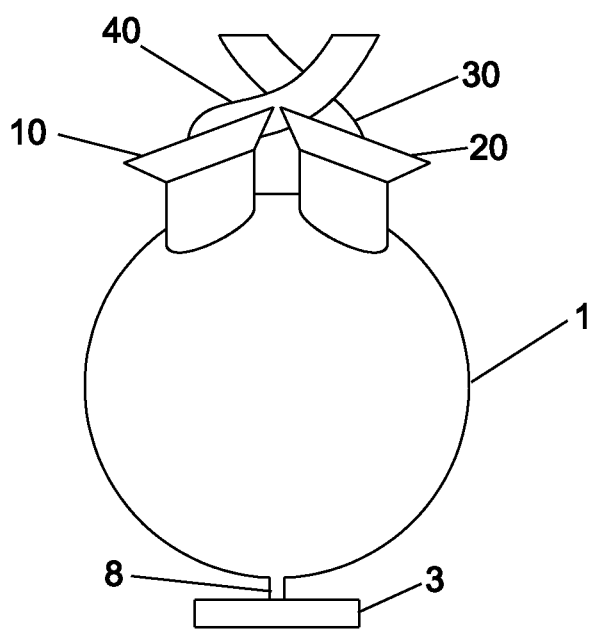
FIG. 6 shows a back elevation view of the artificial autonomous heart, according to an embodiment of the disclosed technology.

FIG. 5 shows a front elevation view of the artificial autonomous heart, according to an embodiment of the disclosed technology. FIG. 6 shows a back elevation view of the artificial autonomous heart, according to an embodiment of the disclosed technology. The body 1 itself may be substantially spherical, such that it appears symmetrical from all directions, notwithstanding the valves and other components extending therefrom.

Figure 7:
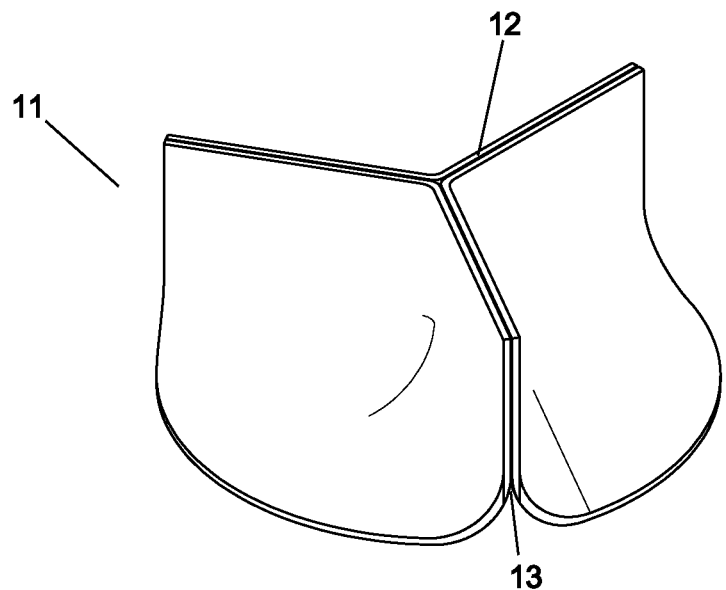
FIG. 7 shows a stand-alone isometric view of a valve used in the artificial autonomous heart, according to an embodiment of the disclosed technology.
Figure 8:
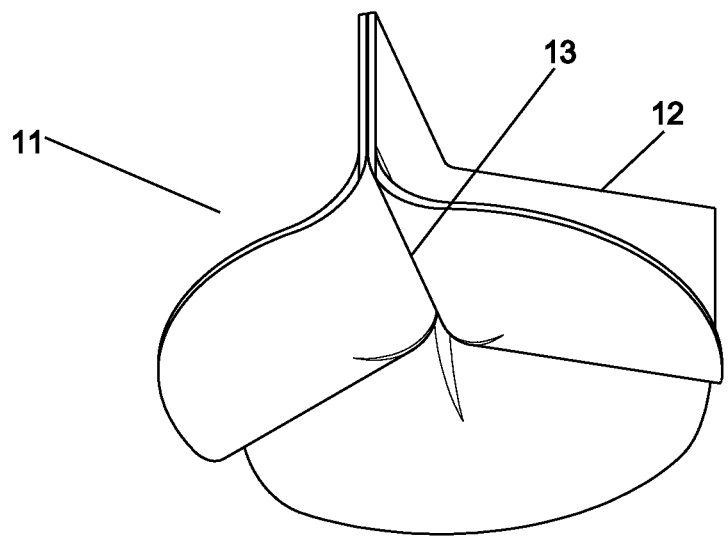
FIG. 8 shows a stand-alone bottom isometric view of a valve used in the artificial autonomous heart, according to an embodiment of the disclosed technology.

FIG. 7 shows a stand-alone isometric view of a valve used in the artificial autonomous heart, according to an embodiment of the disclosed technology. FIG. 8 shows a stand-alone bottom isometric view of a valve used in the artificial autonomous heart, according to an embodiment of the disclosed technology. The valve 11 may be used in the mitral valve 10, the tricuspid valve 20, the pulmonic valve 30 and/or the aortic valve 40. Thus, valve may be designated as "valve 11," "valve 21," "valve 31" or "valve 41," but is described with respect to the mitral valve 10 for explanatory purposes.

Figure 9:
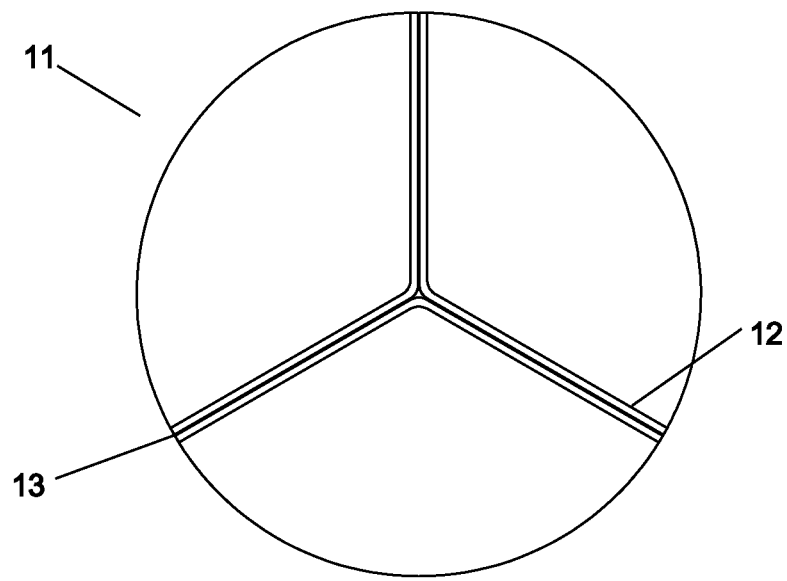
FIG. 9 shows a top plan view of a valve used in the artificial autonomous heart, according to an embodiment of the disclosed technology.
Figure 10:
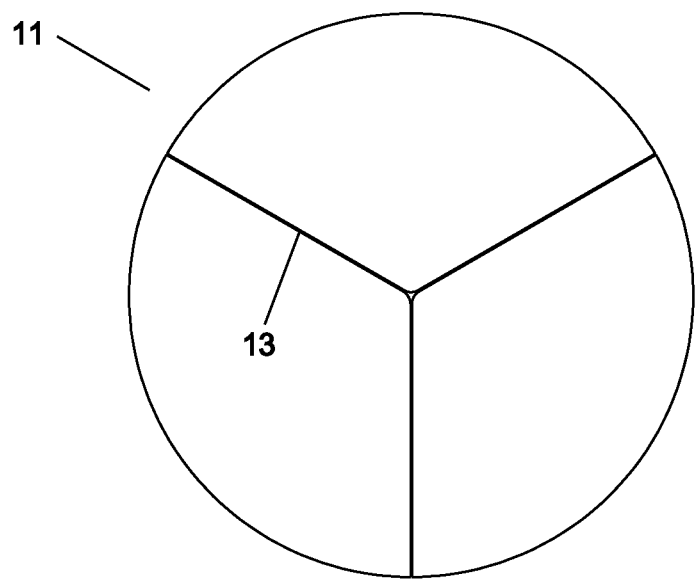
FIG. 10 shows a top bottom plan view of a valve used in the artificial autonomous heart, according to an embodiment of the disclosed technology.

FIG. 9 shows a top plan view of a valve used in the artificial autonomous heart, according to an embodiment of the disclosed technology. FIG. 10 shows a bottom plan view of a valve used in the artificial autonomous heart, according to an embodiment of the disclosed technology. The mitral valve 11 is generally circular, having substantially inclined or vertical lips 12 which are parted to define an opening 13 under pressure of fluid flowing in one direction. Pressure of the fluid causes the lips 12 to part, but does not allow fluid to flow in the opposite direction.

Figure 11:
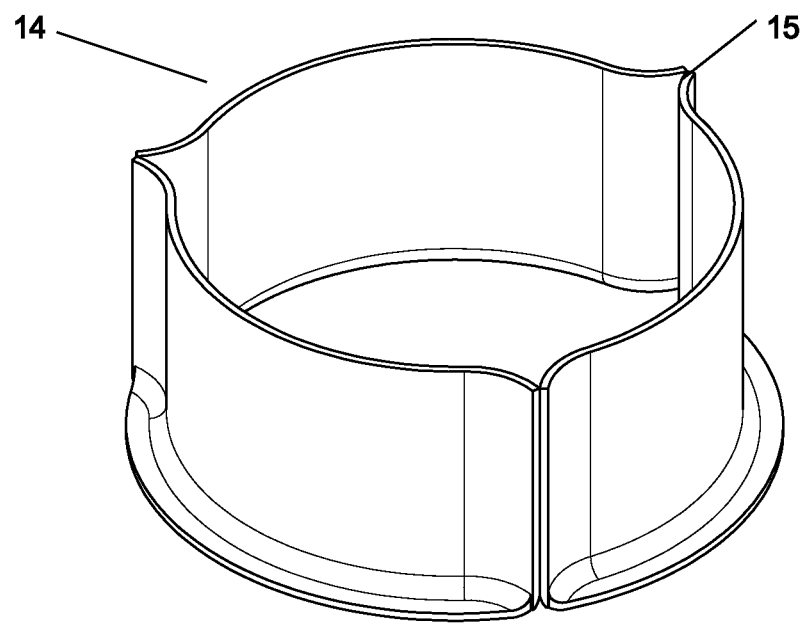
FIG. 11 shows a top perspective view of an open flow port used in the artificial autonomous heart, according to an embodiment of the disclosed technology.
Figure 12:
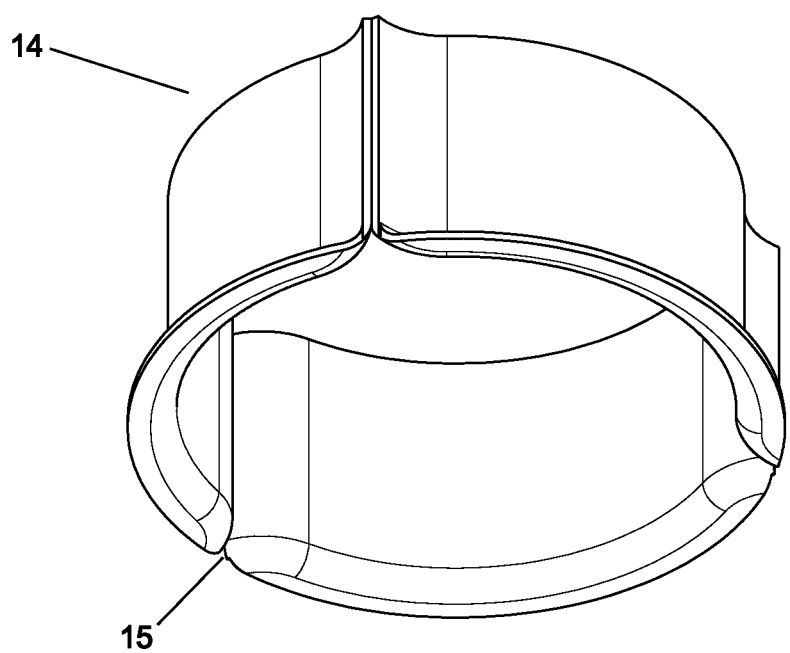
FIG. 12 shows a bottom perspective view of an open flow port used in the artificial autonomous heart, according to an embodiment of the disclosed technology.

FIG. 11 shows a top perspective view of a flow port used in the artificial autonomous heart, according to an embodiment of the disclosed technology. FIG. 12 shows a bottom perspective view of a flow port used in the artificial autonomous heart, according to an embodiment of the disclosed technology. In the position depicted in FIGS. 11 and 12, the flow port is open, under outflow pressure of blood being pumped out of the heart. Slits 15 correspond to the openings 13 in the valve 11.

Figure 13:
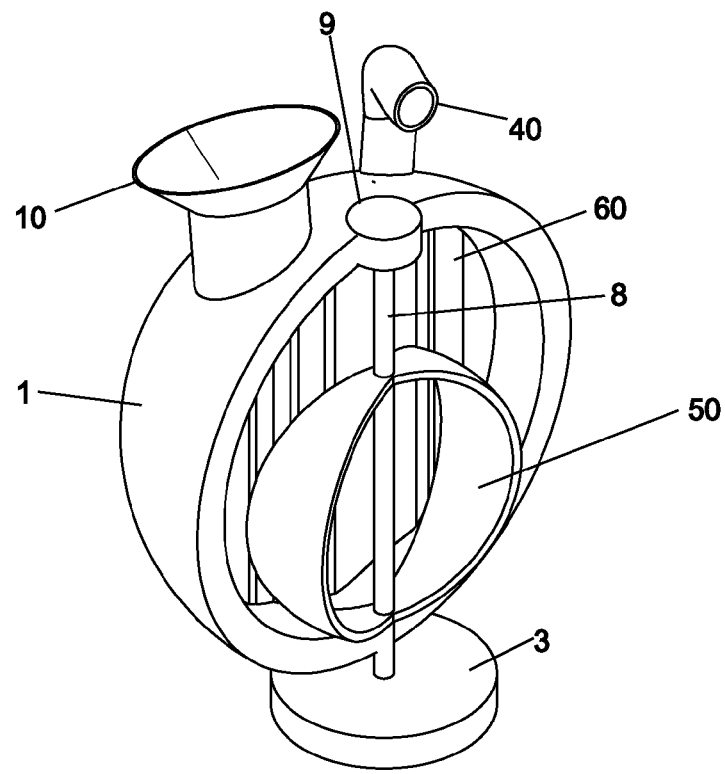
FIG. 13 shows a top plan view of a flow port used in a partial cut-away view of the artificial autonomous heart at diastole, according to an embodiment of the disclosed technology.
Figure 14:
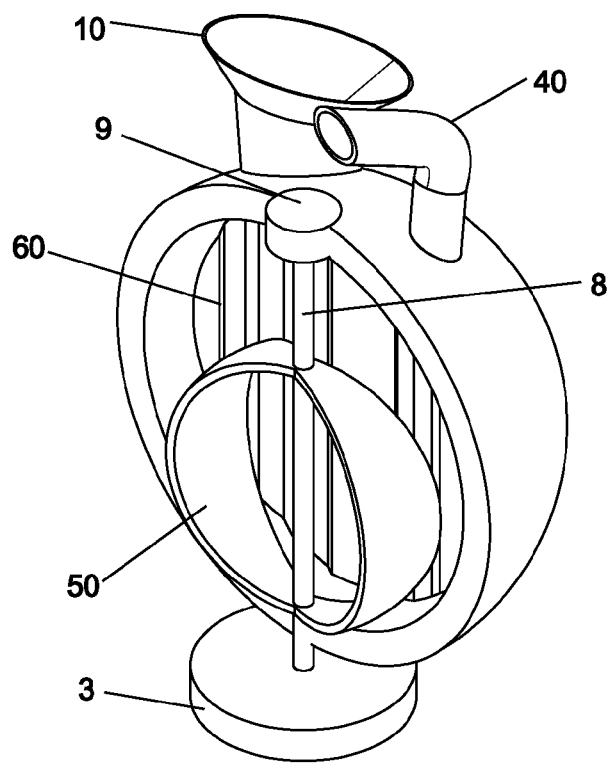
FIG. 14 shows a bottom plan view of a flow port used in another partial cut-away view the artificial autonomous heart at diastole, according to an embodiment of the disclosed technology.

FIG. 13 shows a cut-away view of the artificial autonomous heart in an inflow position, according to an embodiment of the disclosed technology. FIG. 14 shows another cut-away view of the artificial autonomous heart in an inflow position, according to an embodiment of the disclosed technology. Depicted in FIGS. 13 and 14 is a stand-alone view of a single hemisphere of the artificial autonomous heart 1. Thus, the hemisphere has one inflow valve 10 and one outflow valve 40. A turbine-like rotating core 50 is affixed to a shaft 8 inside the artificial autonomous heart 1. The shaft 8 is in turn coupled to the motor 3 to cause the turbine-like core to rotate. A first membrane 60 occupies a large portion of the interior region of the hemisphere. The flow ports 10 and 40 enter directly into the membrane 60. The orientation of the membrane 60 with respect to the rotating core 50 causes the membrane to be methodically filled with blood and then emptied. The other hemisphere (not shown), is essentially a mirror image of the hemisphere shown in FIGS. 13 and 14. Thus, the single rotating core 50 causes both membranes to methodically pump blood.

The turbine-like rotating core 50 inside the sphere 1 turns an entire 360-degrees. As it turns, it pushes the membranes against the domes, effectively ejecting the fluid medium out of the hemispheric ventricles. This duty cycle coincides with a systole of the cardiac cycle. During two-thirds of the cardiac cycle, which coincides with a diastolic phase of the cardiac cycle, the turbine-like rotating core rests parallel to the membranes. This allows the hemispheric ventricles to fill up, before it makes another sweep for the next cardiac cycle.

Each hemispheric ventricle has two one-way valves oriented in opposite direction to each other. When one opens, the other closes, ensuring a one-direction flow of fluid medium. The rotating turbine 50 in the core is connected to the motor shaft 8 of the brushed or brushless motor 3 located outside the sphere 1. Lubricating fluid, such as vegetable oil, in the milieu of the rotating core 50 may facilitate a reduction in frictional movement of the turbine against the elastic membranes. The moving core 50 is uniformly stabilized during rotation at the base and apex of the sphere 1 by ball bearings (not shown). A 9-12-volt lithium polymer battery supplies the power to the brushed or brushless DC motor.

Figure 15:
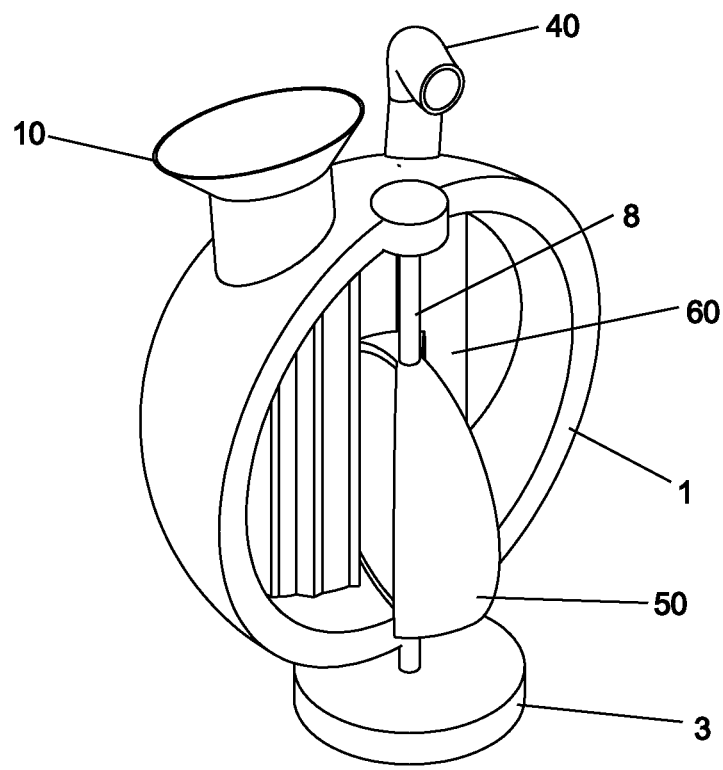
FIG. 15 shows a partial cut-away view of the artificial autonomous heart at systole, according to an embodiment of the disclosed technology.
Figure 16:
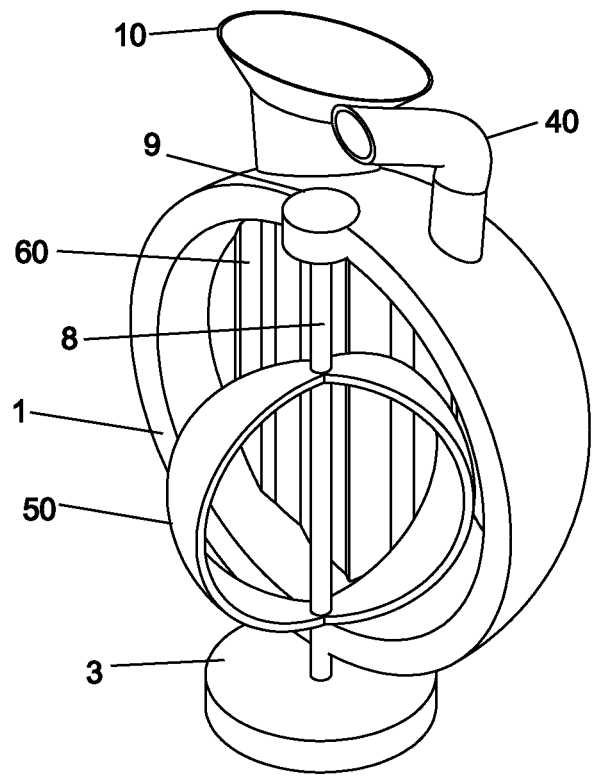
FIG. 16 shows another partial cut-away view of the artificial autonomous heart at systole, according to an embodiment of the disclosed technology.

FIG. 15 shows a cut-away view of the artificial autonomous heart in an outflow position, according to an embodiment of the disclosed technology. FIG. 16 shows another cut-away view of the artificial autonomous heart in an outflow position, according to an embodiment of the disclosed technology. The two domes represent, and correspond to, the two ventricles of a human heart. Each dome comprises one unitary sphere 1. The sphere 1 is oriented such that the top will be called the base of the domes from which the contiguously arranged flow ports and valves arise, and bottom will be called the apex from where the motor 3 engages the rotating core of the sphere 1. Each dome contains an elastic membrane 60, 62, which separates the right ventricle and left ventricle. The space between the membrane 60 and sphere 1 accommodates in transit blood volume coming in through the inflow valves, tricuspid valve, and mitral valve from the right and left atria, respectively. Blood exiting through the outflow valve conduits pulmonic valve from the right ventricle to the pulmonary artery and through the aortic valve from the left ventricle to the aorta.

Figure 17:
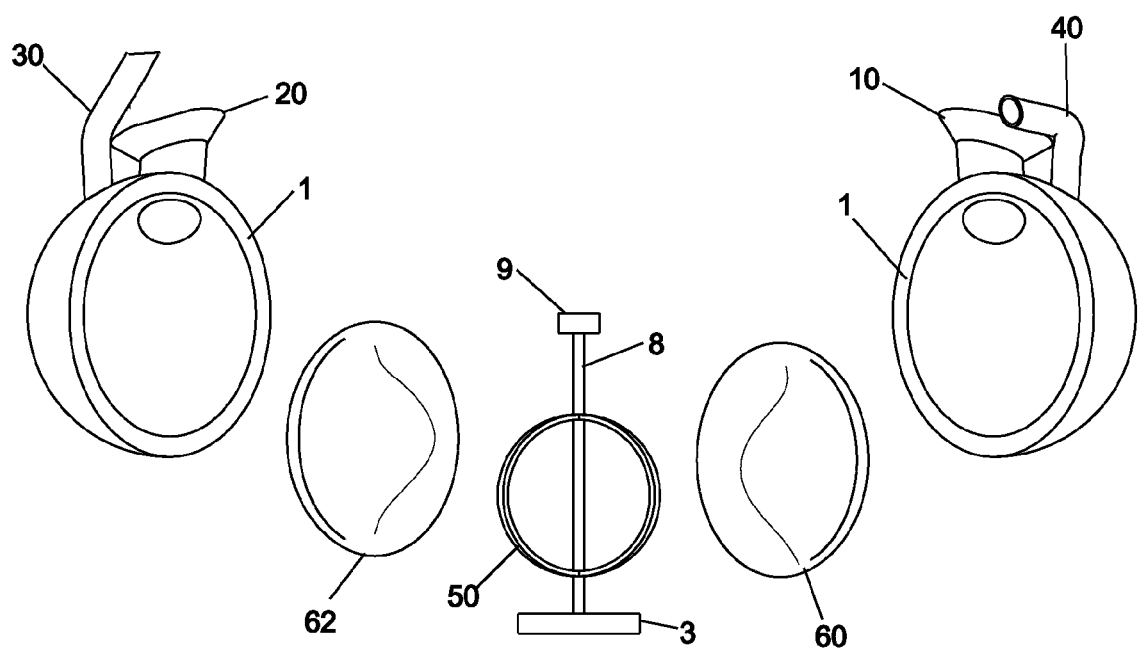
FIG. 17 shows an exploded view of the components of an artificial autonomous heart, according to an embodiment of the disclosed technology.

FIG. 17 shows an exploded view of the components of an artificial autonomous heart, according to an embodiment of the disclosed technology. The rotating core assembly comprises two arched turbines and scalloping inter-space, the shaft 8, which at one end engages the ball-bearing stabilizer 9, and the rotor of the brushless motor 3 on the opposite end. The two arched turbines 50 on either side form a planar circumference with the rotor shaft 8. During a systole these turbines 6 push the membranes 60 and 62 against domes 1. Inflow valves 10, 20, and outflow valves 30, 40 are also shown.

The scalloping interval between the turbines 6 allows blood to enter the membranes 60 and 62 as the turbines on opposing quadrants pass the membranes 60 and 62. This is the diastolic phase of the cardiac cycle. The blood propulsion is achieved by the longitudinal rotation of the core assembly. The core assembly rotates between the membranes of the ventricles, which essentially touch each other back to back when the ventricles are full. As the turbines 50 on opposite quadrants of the core pass under the membranes, they push the membranes 60, 62 against the dome squeezing out the blood volume.

After the turbines 50 pass the membranes 60, 62 in one complete turn, the core assembly stops, and, in this resting phase, the turbines 50 are situated on the sides of the membranes 60, 62. The scalloping inter-space between the arched turbines is situated between the membranes 60, 62, allowing the ventricles to fill up. The rotation is quick and completes a 360-degree turn. Then, the core assembly rests twice the length of time after each complete turn. This allows more time for blood to fill in the ventricles. A cardiac cycle includes a rapid complete turn, or propulsion phase, and a resting phase twice the length of time. The propulsion phase takes only one-third of the time of a cardiac cycle.

Figure 18:
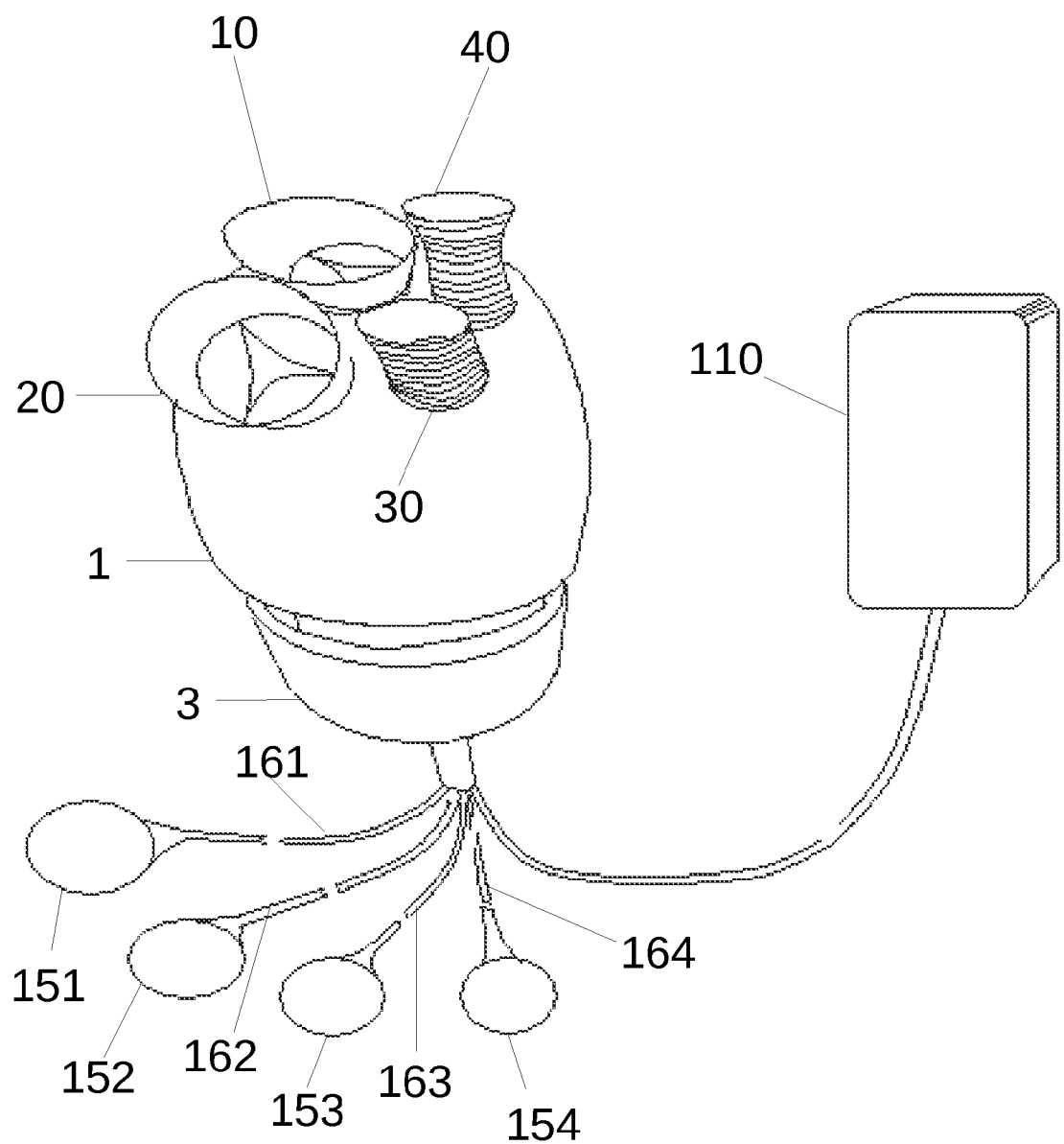
FIG. 18 shows a general overview of the components of an artificial autonomous heart system, according to an embodiment of the disclosed technology.

FIG. 18 shows a general overview of the components of an artificial autonomous heart system, according to an embodiment of the disclosed technology. This figure illustrates, in perspective, the basic components and their connections to the remnants of the excised heart. The main components include the artificial heart body 1, the motor 3, a battery 110, and a plurality of sensors 151-154. The mechanical heart 1 and its inflow and outflow valve conduits are controlled by the motor 3. The motor 3 may be a brushless DC motor, housed in a compartment, along with a built-in microprocessor. The battery 110 may be a rechargeable lithium ion battery disposed on the patient. The battery 110 may be a totally implantable 9-volt battery (such as a lithium polymer battery), which powers the motor. It is implanted outside the pericardium and near the skin surface. It is designed to be transcutaneously rechargeable.

The sensors 151-154 may include a pressure sensor 151, a tilt sensor 152, a vibration sensor 153, and/or a temperature sensor 154. The sensors 151-154 may be strategically placed at different parts of the body, in order to detect various stimuli which will affect the operation of the artificial heart.

Figure 19:
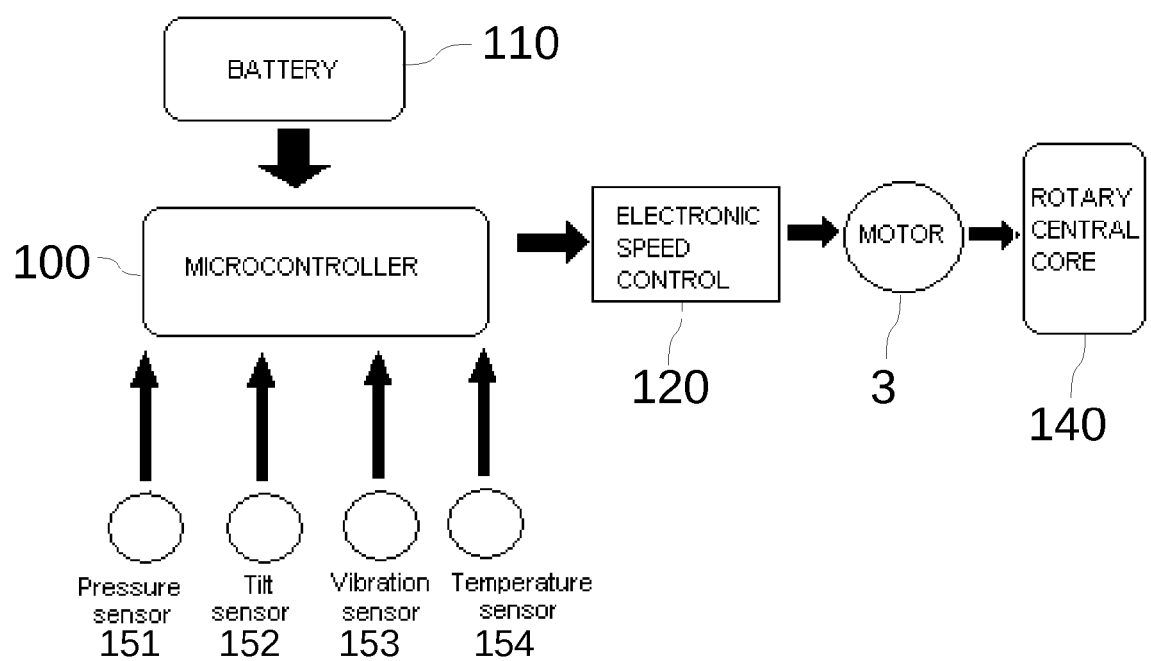
FIG. 19 shows a block diagram of the system components of the artificial autonomous heart, according to an embodiment of the disclosed technology.

FIG. 19 shows a block diagram of the system components of the artificial autonomous heart, according to an embodiment of the disclosed technology. As depicted, the battery 110 is connected directly to the microcontroller 100. The microcontroller 100 may be located within the motor 3, the spherical body 1, or the battery 110. The microcontroller 100 is coupled to an electronic speed controller 120 which, in turn, dictates the speed of the motor 3. The motor 3 is directly coupled to the rotary central core 140. The plurality of sensors 151-154 is coupled to the microcontroller 100.

As illustrated in FIG. 19, the microcontroller 100 directly connects with the motor 3. The microcontroller 100 is the nerve center of the autonomous artificial heart. It receives electrical signals from four sensors. The pre-programmed algorithm processes the electronic signals from the sensors and then activates the potentiometer, which basically controls the speed of the motor.

A code written in a programming language, such as C, is programmed into the microcontroller 100, using a computer (not shown). The computer may employ the Arduino Integrated Device Environment to communicate with the microcontroller 100. The pre-programmed code initially sets the RPMs of the rotating central core. The rest of the code sets the parameters when the central core should rotate faster or slower then 100 rpm. These parameters include the threshold as to when to activate the pressure sensor placed on or around the aorta, or when the torso is upright, or when the body moves around like when running, or when the body temperature rises.

The microcontroller 100, with its encoded algorithm, translates all these activity parameters into performance of the mechanical heart. For example, cardiac output increases by increasing the cardiac cycle when the body is in upright posture, or when an activity such as running is detected. On the other hand, for example, the cardiac cycle is set back to default mode when standing or lying down is detected by the tilt sensor 152.

The microcontroller may alter the motor speed in response to signals from touch, pressure and tilt-sensing sensors. Other sensors may potentially be employed, including temperature and activity sensing. The microcontroller 100, may be an Arduino UNO microcontroller employing a computer language similar to C+. Other Arduino models that could carry out more complicated programs may alternatively be employed. Possible options for microcontrollers may also include Matlab or Simulink.

The microcontroller may be configured to activate the sensors 151-154. For example, the touch sensor or transducer may be caused to activate at approximately 4 psi or 200 mm Hg. When the desired pressure is reached, the program could translate the pressure variable into activating the microcontroller as an actuator to reduce the rotary speed of the motor. The same scenario would apply for the tilt sensor. When the person, and therefore, the sensor is upright, the tilt sensor causes the microcontroller to increase the motor speed compared to the horizontal position. Then when going back to a lying position, as detected by the tilt sensor, the motor speed may decrease or slowsdown to baseline setting.

The rotary speed of the motor should be programmed at a baseline of 100 revolutions per minute (RPM). This speed would be equivalent to a normal resting heart rate or cardiac cycle. However, this baseline is assumed to be arbitrary at this point. The workload in the mock circulation and resistance, such as like friction between the rotating core of the artificial heart and the elastic membranes, will determine the rotary speed of the motor. In addition, lubrication in the artificial heart model will need to be taken into consideration. Further, these experiments should provide data to determine the most suitable motor.

Pulse-width modulation (PWM) in the Arduino UNO may be written into the integrated circuit. If, for example, the heart normally beats 60 times a minute, or one beat per second, then PWM could be set with a duty cycle at 333 milliseconds to represent a systole of the cardiac cycle. The remaining 667 milliseconds of the cardiac cycle would be the diastolic phase.

In a simpler embodiment, a two-gear system might be used. However, use of gears should be minimized for long-term use due to an eventual reduction in efficiency, and therefore this approach should not be considered as a long term solution. In this embodiment, the motor turns the rotating core of the artificial autonomous heart one revolution every third of the cardiac cycle, PWM may not be required since the two-gear system is designed to also create a duty cycle. The motor would not switch off or stop as it would during PWM. Rather, the motor would continuously turn, while the programmed sensors regulate its speed.

As shown in FIGS. 18 and 19, several sensors 151-154 may be wired directly to the microcontroller 100 from their strategic locations. These sensors transform the stimuli from a surrounding environment and transform it into electronic signals which influence the functions of the autonomous artificial heart. These sensors may include a pressure sensor 151. The pressure sensor 151 may be located on or around the ascending aorta. The pressure sensor 151 may be a transducer which is set to trigger like a touch sensor that sends electrical signals to the microprocessor 100 when a certain level of blood pressure is reached.

Another sensor is the tilt sensor 152, which determines the posture of the body. The tilt sensor 152 may be, for example, an accelerometer. When the body is lying down, the tilt sensor is deactivated. When the body is upright, the sensor is activated, and an electrical signal is received and processed by the nerve center to speed up the motor 3.

The vibration sensor 153 interprets a piezo-electric signal, and sends the signal to the microcontroller 100 when the body starts walking or moving. No signal occurs when the body is at rest. The temperature sensor 154 converts analog readings of core body temperature to digital signals to be interpreted by the microcontroller 100. The signals, may, for example, cause the motor 3 to increase RPMs when the body temperature increases.

The mechanical heart has its rotating central core engaged to the rotor of the 9 to 12 volt brushless motor regulated by pulse wave modulation or a servomotor. The electronic speed control regulates the speed of the motor via the microcontroller, which in turn receives signals from the four sensors.

The motor rotates the central core to 360-degrees. The speed of rotation is programmed using the pulse width modulation, such that the high output voltage is 30% and the delay or zero output is 70% of the duty cycle. The delay allows the ventricles to fill up (diastolic phase of cardiac cycle). The quick and short-duration high output voltage enables a forceful ejection of the stroke volume (systolic phase of the cardiac cycle).

The battery 110 may be an implantable battery, which powers the motor. It may be implanted outside the pericardium and near the skin surface. It is designed to be transcutaneously rechargeable. Additionally or alternatively, the battery 110 may be charged via a radio frequency recharging pad. Such would allow the battery to be charged by placing a charging pad in the proximity of the battery on the surface of the skin. In practice, a metal conductor of the pad that is connected to a 110 volt-AC power outlet could be placed over the rechargeable DC lithium battery. The rechargeable lithium battery may be implanted in the body like a permanent pacemaker in a pocket on the pectoralis of the chest. Externally, the radio frequency charging pad is laid over it during re-charging. Use of electric conducting gel with this TETS (transcutaneous electronic transfer system) minimizes risk of possible injury to the skin. TETS has been proven to be a safe method during defibrillation in cardiac arrest, delivering 200 joules through the chest wall.

Other modalities of TETS, such as short pulses of microwave through the skin, may be possible. For example, is it possible to create pulses of microwave energy? How short a pulse wave in conjunction with a conducting medium may optimize TETS without burning the skin? The feasibility of this approach should be evaluated.

Figure 20:
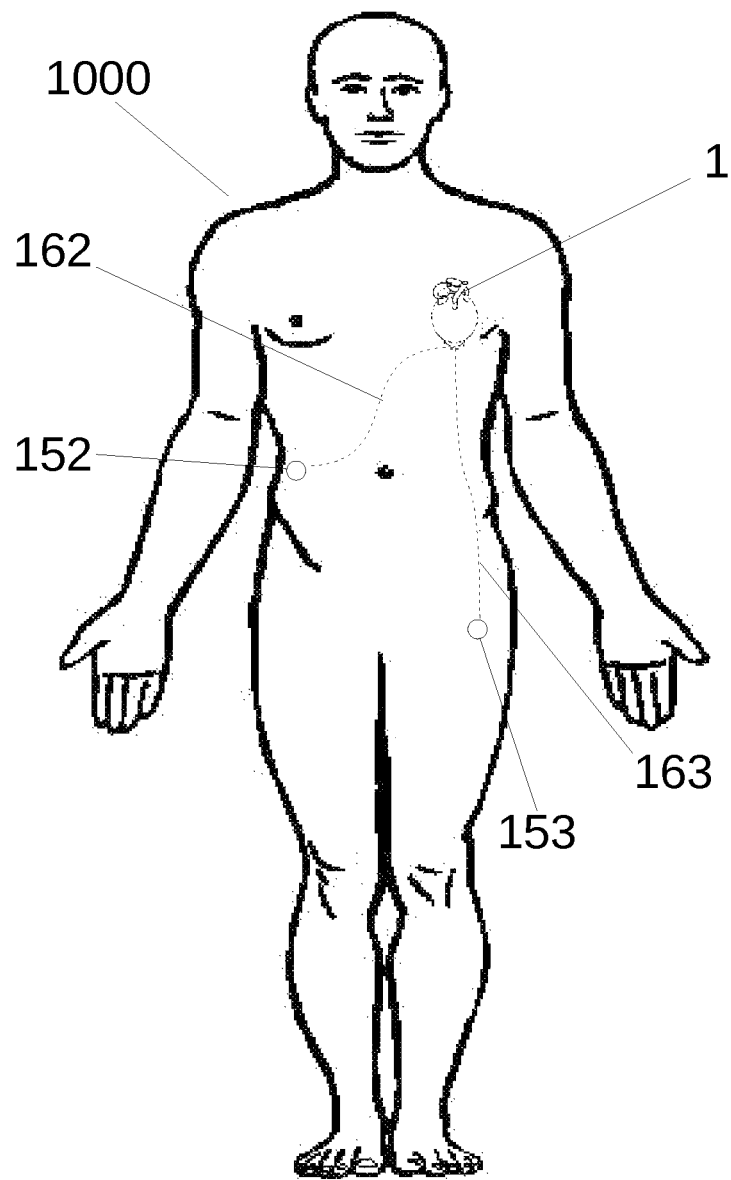
FIG. 20 shows a diagram of a human body with an exemplary sensor arrangement of an implanted artificial autonomous heart, according to an embodiment of the disclosed technology.

FIG. 20 shows a diagram of a human body with an exemplary sensor arrangement of an implanted artificial autonomous heart, according to an embodiment of the disclosed technology. The patient 1000 is shown with the approximate location of the implanted artificial heart 1. Wires 162 and 163 are extended from the artificial heart 1. The wires 162 and 163 may be implanted during the same procedure as the implantation of the artificial heart 1. One of the wires 162 extends to a tilt sensor 152 disposed in the lower torso of the patient 1000. The position of the tilt sensor 152 is such that the orientation of the patient is detectable. Thus, the tilt sensor 152 may detect if the person is standing, or sitting upright, or lying down, in order to communicate to the artificial heart 1 an appropriate heart rate. Other sensors (not shown) may be placed throughout the body to detect various stimuli which can dictate or affect the rate of pumping of the artificial heart 1.

Another wire 163 extends downwards from the artificial heart 1 towards the hips of the patient 1000. This wire 163 is connected to a vibration/movement sensor 153 in the hip region. The sensor 153 detects whether the patient 1000 is walking, running, and/or performing any other strenuous activity. The degree of movement detected by the vibration sensor 163 communicates to the artificial heat 1 the necessary heart rate to sustain such activity.

Figure 21:
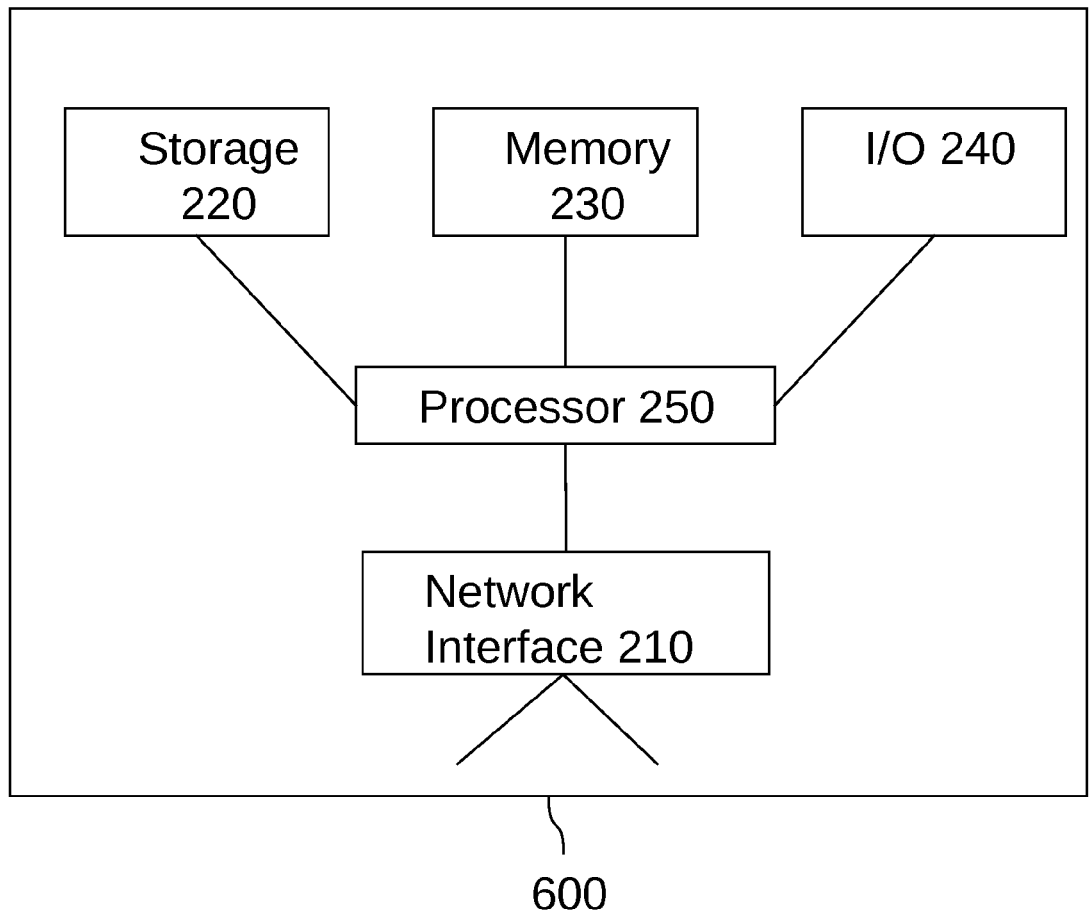
FIG. 21 shows a high-level block diagram of a device that may be used to carry out the disclosed technology.

FIG. 21 shows a high-level block diagram of a device that may be used to carry out the disclosed technology. Device 200 comprises a processor 250 that controls the overall operation of the computer by executing the device's program instructions which define such operation. The device's program instructions may be stored in a storage device 220 (e.g., magnetic disk, database) and loaded into memory 230 when execution of the console's program instructions is desired. Thus, the device's operation will be defined by the device's program instructions stored in memory 230 and/or storage 220, and the console will be controlled by processor 250 executing the console's program instructions.

A device 200 also includes one or a plurality of input network interfaces for communicating with other devices via a network (e.g., bluetooth). The device 200 further includes an electrical input interface for receiving power and data from the battery 110. A device 200 also includes one or more output network interfaces 210 for communicating with other devices. Device 200 also includes input/output 240 representing devices which allow for user interaction with a computer (e.g., display, keyboard, mouse, speakers, buttons, etc.). One skilled in the art will recognize that an implementation of an actual device will contain other components as well, and that FIG. 20 is a high level representation of some of the components of such a device for illustrative purposes. It should also be understood by one skilled in the art that the method and devices depicted in FIGS. 1 through 20 may be implemented on a device such as is shown in FIG. 21.

Figure 22:
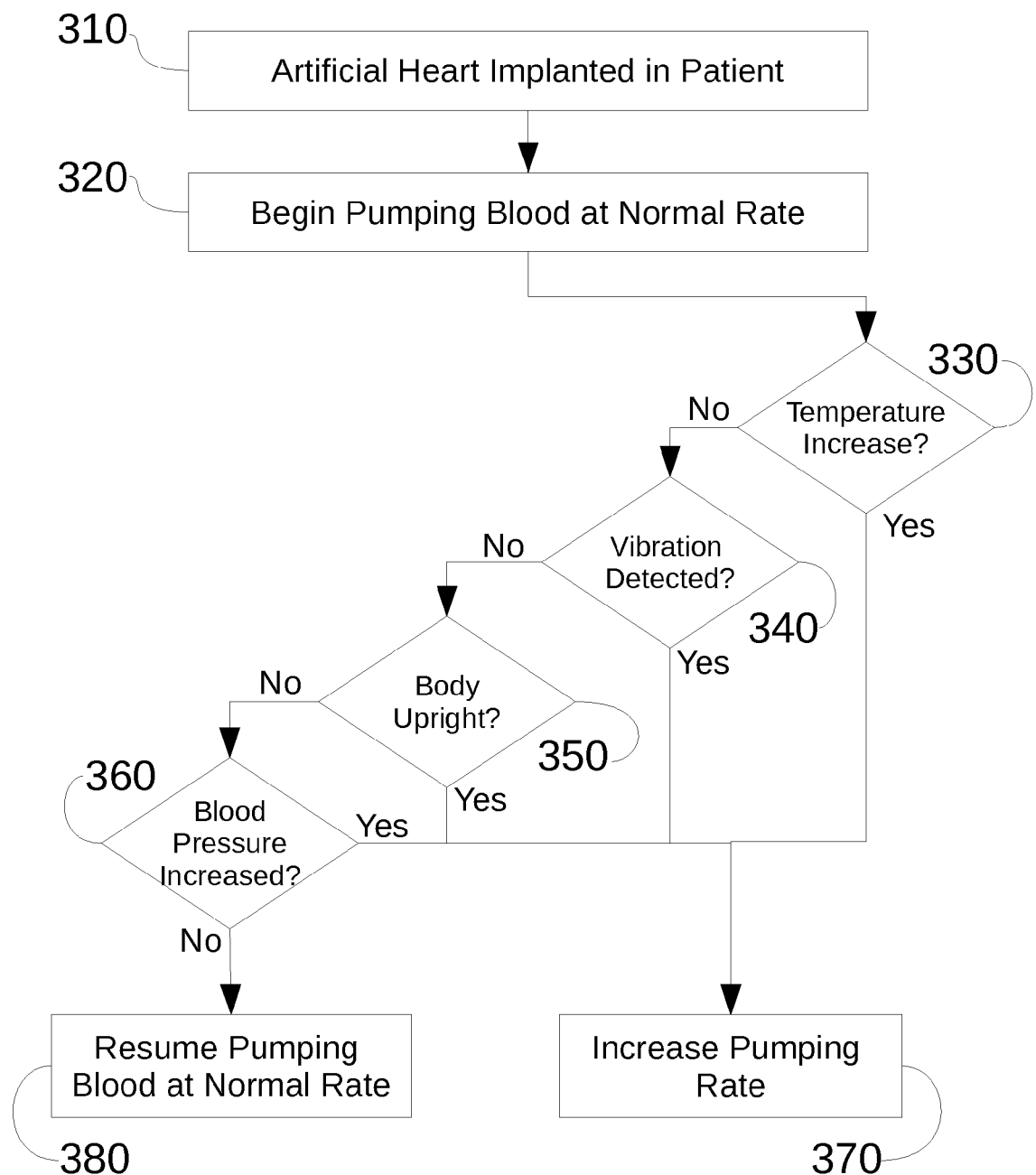
FIG. 22 is a flow chart outlining the steps taken in an exemplary method of carrying out the disclosed technology, according to an embodiment of the disclosed technology.

FIG. 22 is a flow chart outlining the steps taken in an exemplary method of carrying out the disclosed technology, according to an embodiment of the disclosed technology. The method begins in step 310, whereby the artificial heart is implanted into a patient. This is carried out through a major surgical operation. The sensors are properly placed at the relevant regions of the body. The lithium battery is also implanted in the body to provide power to the artificial heart. Once installed, the artificial heart is configured to begin pumping blood in step 320 at a normal rate. The artificial heart is constantly monitored and managed by the microprocessor, which is constantly receiving feedback from the plurality of sensors. Any changes detected by the sensors in the subsequent steps 330 through 360 result in changes to the pumping rate of the artificial heart. Thus, every stimulus detected results in the motor increasing the pumping rate, decreasing the pumping rate, or maintaining the current rate.

The example shown in FIG. 21 is merely provided for explanatory purposes, and is but one sensor configuration. The steps 330 through 360 may be performed contemporaneously, one after another, or in order of preference or priority. In the example, the temperature sensor detects if there is a temperature increase in step 330. If a temperature increase is detected, the pumping rate is increased in step 370 to adjust to the temperature increase. In a further embodiment, the pumping rate may be decreased if a lower temperature is detected. Thus, the pumping rate may be correlative to the patient's internal body temperature, all other factors being constant.

In the next step, step 340, the existence of vibrations is detected by the vibration sensor. The method proceeds with step 350, whereby the tilt sensor 350 detects the position of the body of the patient. That is, the tilt sensor determines whether the patient is upright or lying down. If the patient is upright, the microcontroller causes the pumping to increase in step 370. If the patient is lying down, the pumping rate resumes in step 380. Alternatively, if the patient is lying down, the pumping rate may be decreased.

Next, in step 360, the pressure sensor detects any changes in blood pressure and causes the microcontroller to act accordingly. If blood pressure increases or shows a spike, the motor causes blood to be pumped at an increased rate. Alternatively, a decrease or normal blood pressure reading could result in the artificial resuming a normal pumping rate or decreasing the pumping rate. The sensors may constantly be monitored, and any fluctuations automatically reflected in the pumping rate. Thus, for example, if at a given moment, a patient is lying down dormant, but experiencing a spike in blood pressure and temperature, the detected changes may offset one another based on the particular parameters for the patient. However, if, for example, a patient is prone to heart attacks, an increase in blood pressure may take precedence over the readings detected by the other sensors and may therefore be more controlling of the pumping rate.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the invention.

We claim:

1. An artificial heart with a microcontroller pacemaker, said pacemaker configured to activate a systole in said artificial heart based on the receipt of data from sensors, said sensors comprising:
    a pressure sensor;
    an orientation sensor;
    a vibration sensor indicating that a threshold level of vibration or muscle movement has been reached; and
    a temperature sensor;
    wherein upon said systole being activated upon a passage of a pre-determined amount of time and a determination that pumping blood from said heart to said body is timely, based on input from at least one said sensor.

2. The artificial heart of claim 1, wherein said microcontroller sets said rate of systole at a default rate in the absence of stimuli to the contrary, and begins to return said rate of said systole to said default rate upon said absence of stimuli.

3. The artificial heart of claim 1, wherein said default rate corresponds to a 100 RPM rate of rotation of said longitudinal member.

4. The artificial heart of claim 1, wherein pressure above a pre-defined threshold causes said determination to be made to decrease or increase the rotation of the longitudinal member and increase pumping volume.

5. The artificial heart of claim 1, wherein an upright orientation, as detected by said orientation sensor, causes a systole to be activated more frequently than a lying down orientation.

6. The artificial heart of claim 1, wherein increased vibration, as detected by said vibration sensor, causes a systole to be activated more frequently up to said pre-determined minimum amount of time between pumping.

7. The artificial heart of claim 1, wherein increased temperature, as detected by said temperature sensor, causes a systole to be activated more frequently than a minimum amount of time between pumping.

* * * * *